United States Patent
Alonzo

Patent Number: 5,253,661
Date of Patent: Oct. 19, 1993

[54] COMPOSITE ORAL CLEANING APPARATUS

[76] Inventor: Harold Alonzo, P.O. Box 191 (9-¼Mile Marker on Hwy. 11), Kurtistown, Hi. 96769

[21] Appl. No.: 944,436

[22] Filed: Sep. 14, 1992

[51] Int. Cl.$^5$ ............................................. A61C 15/00
[52] U.S. Cl. .................................................... 132/321
[58] Field of Search ....................... 132/321, 323, 329; 433/143

[56] References Cited

U.S. PATENT DOCUMENTS

| | | | |
|---|---|---|---|
| 407,362 | 7/1889 | Mason | 132/321 |
| 469,064 | 2/1892 | McKay | 132/321 X |
| 2,059,287 | 11/1936 | Storm | 132/323 |
| 2,192,733 | 3/1940 | Bader, Jr. | 132/321 X |
| 2,552,134 | 5/1951 | Berliner | 433/143 |
| 3,605,765 | 9/1971 | Canby | 132/329 |
| 3,954,115 | 5/1976 | Bergtsson | 132/329 |
| 4,616,667 | 10/1986 | Tang | 132/329 |
| 4,805,646 | 2/1989 | Shimenkov | 132/329 |
| 4,942,034 | 7/1990 | Hill et al. | 132/321 X |
| 5,127,833 | 7/1992 | Kline | 433/143 |

FOREIGN PATENT DOCUMENTS 3130971 2/1983 Fed. Rep. of Germany ...... 132/321

*Primary Examiner*—Gene Mancene
*Assistant Examiner*—Nicholas D. Lucchesi
*Attorney, Agent, or Firm*—Blakely, Sokoloff, Taylor & Zafman

[57] ABSTRACT

The present invention provides a teeth cleaning apparatus which is a composite of oral cleaning implements. An elongated member has one pointed tip for cleaning between the teeth and a second end having a scoop shape for dislodging particulate matter from hard to reach places. The extended shaft portion of the device provides for supporting and handling of the scoop and point-end. Alternative embodiments of the present invention further provide a spool or cleat region cut into the elongated shaft. The spool or cleat section provides a region along the shaft suitable for wrapping and holding a supply of dental floss. The materials used in the proposed device are selected so as to minimize the amount of discomfort resulting from interacting with the gums and may be any color and optionally flavored.

16 Claims, 1 Drawing Sheet

COMPOSITE ORAL CLEANING APPARATUS

BACKGROUND OF THE INVENTION

1. Field of the Invention

The present invention relates to an apparatus for cleaning between teeth and surrounding areas in the mouth. More particularly, the present invention relates to a composite tool for dislodging particles between teeth as well as from other areas in the mouth which accumulate food and other debris.

2. Art Background

Conventional toothpicks are well-known and are recognized as rigid pieces of wood or plastic sharpened to a point at one or both ends. Conventional toothpicks are used for cleaning out debris, specifically between teeth, by poking and wedging the toothpick point between the teeth so as to dislodge accumulated particulate matter. The pointed ends of conventional toothpicks are not particularly useful for cleaning other portions of the mouth such as the areas between the gums and cheek and behind the farthest teeth.

Conventional toothpicks suffer a number of disadvantages despite their wide use and application. The pointed tip can be hazardous in that careless use may puncture a gum or cut inner portions of the mouth. Further, the use of a pointed tip often proves ineffective for dislodging food particles from the other hard to reach regions of the mouth because the tip itself is hard to maneuver to an exact location and is not effectively used as a scoop. Often, to clean portions of the mouth other than between teeth, it is necessary to resort to a finger or other oral implement or rinse which may not always be convenient.

It would be a great advantage and, is therefore an object of the present invention, to provide an oral cleaning device which is suitable for both cleaning between teeth and for other areas inside the mouth.

SUMMARY OF THE INVENTION

It is an object of the present invention to provide a composite device for cleaning between teeth and other areas of the mouth for which conventional toothpicks are not suited.

It is also an object of the present invention to provide a device which may be used for cleaning between teeth with less risk of gum damage upon insertion than is available from conventional toothpicks.

It is further an object of the present invention to provide an apparatus which may be used for massaging gums in addition to providing cleaning functions.

It is still another object of the present invention to provide a composite oral cleaning apparatus which includes a mechanism suitable for holding and dispensing a supply of dental floss.

It is also an object of the present invention to provide a cleaning implement which provides the flexibility to access hard to reach places so that they are more easily cleaned.

These and other objects of the present invention are provided in a composite oral cleaning apparatus in which an elongated member has one pointed tip for cleaning between the teeth and a scoop-shaped end for scraping other mouth regions. The elongated shaft portion of the device may be more rigid than the scoop and/or point end to provide for greater support and handling. Alternative embodiments of the present invention further provide either a cut-away spool section or a cleated region cut into the elongated shaft. These sections provide a region along the shaft suitable for wrapping and holding a supply of dental floss. The materials used in the proposed device are selected so as to minimize the amount of discomfort resulting from interacting with the gums.

BRIEF DESCRIPTION OF THE DRAWINGS

These and other objects of the present invention will be described with respect to the following figures in which.

DETAILED DESCRIPTION OF THE INVENTION

Figure 1:
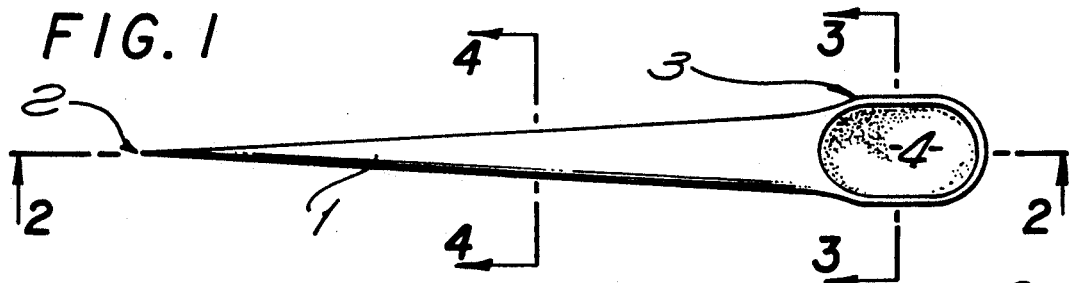
FIG. 1 illustrates a first embodiment of the oral cleaning apparatus in accordance with the present invention.
Figure 2:
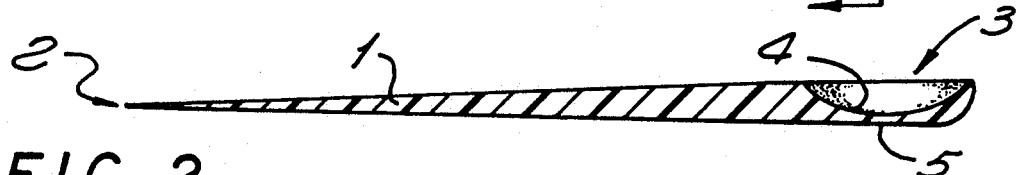
FIG. 2 is a cross-sectional view taken on line 2—2 of FIG. 1.
Figure 3:
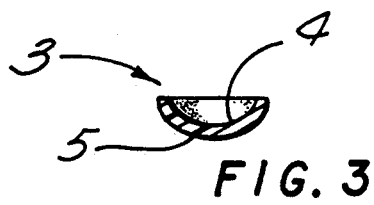
FIG. 3 is a cross-sectional view taken on line 3—3 of FIG. 1.
Figure 4:
FIG. 4 is a cross-sectional view taken on line 4—4 of FIG. 1.

A composite apparatus is described which is useful for cleaning between teeth in the manner that conventional toothpicks are used. The teeth cleaning portion of the present invention also serves as a useful tool for massaging gums which strengthens them. An additional aspect of the present invention is the inclusion of an implement for cleaning areas of the mouth other than between teeth. These areas include the region of the mouth between the gums and cheeks where it is known that food can become lodged with no easy or "socially polite" method of removal.

Referring now to FIGS. 1-4 a first embodiment of the present invention is illustrated along various axes. In this first embodiment, an elongated and tapered central shaft 1 having an elliptical cross-section is provided for supporting the various oral implements of the present invention. The elongated shaft 1 is molded of rigid but flexible material such as plastic or rubber or other material having similar characteristics. The shaft 1, in addition to providing support for the oral cleaning tools also serves as a handle which the user of the apparatus holds for positioning and utilizing the invention. The length of the shaft is essentially arbitrary, needing only to be long enough to be held for reaching into the mouth, but not so long as to be inconvenient to package or carry. In the first embodiment, it has been found that a length of approximately 2-2½" satisfies these requirements.

The first embodiment of the invention shown in FIGS. 1-4 has cleaning implements at the two ends of the rigid shaft 1. At one end is the pick tool 2 which in the first embodiment is the fully tapered end of the shaft 1. The pick tool 2 is used to clean between teeth in a manner similar to that employed when using a conventional toothpick. The user grasps the rigid shaft 1 and positions the tip of pick tool 2 between the desired teeth and gently inserts and retracts the tip until whatever particulate matter present is dislodged. Because the tip of pick tool 2 is the extended tapered end of the rigid shaft 1, it is more flexible than wooden toothpick ends and less likely to cause gum damage. Further, in addition to being useful for cleaning between teeth, the pick tool 2 may be used for gentling massaging the gums of the user. The pick tool 2 may optionally comprise a second, softer material and be affixed to the rigid shaft 1 by bonding or other appropriate means.

At the opposite end of the rigid shaft 1 of the first embodiment of the present invention shown in FIGS. 1-4 is a second oral cleaning implement, the "mouth scoop" 3. The scoop 3 has a rounded rectangular shape that is wider than the rigid shaft 1 at its widest point, but having approximately the same depth. The scoop 3 is made of the same molded material of the shaft 1 but may optionally be a softer material as described with reference to the pick tool 2 to further provide comfort when it is utilized inside the mouth. The scoop tool 3 has two surfaces 4 and 5. In the first embodiment illustrated in FIGS. 1-4, the surface 4 is concave and the surface 5 is slightly convex. The overall shape of the scoop 3 in the first embodiment thus resembles a spoon. The scoop tool 3 is used to clean in those hard-to-reach places such as between the gums and cheeks where food is known to become lodged. As when the pick tool 2 is used, the scoop tool 3 is used by the user holding the rigid shaft 1 and positioning the scoop tool 3 to the appropriate position and gently scraping to dislodge whatever particulate matter is present.

Figure 5:
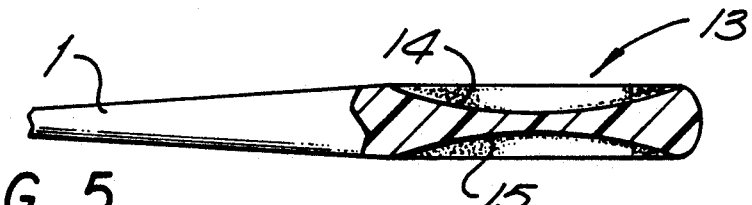
FIG. 5 illustrates a portion of FIG. 2 showing an alternative embodiment of the oral cleaning apparatus in accordance with the present invention.
Figure 6:
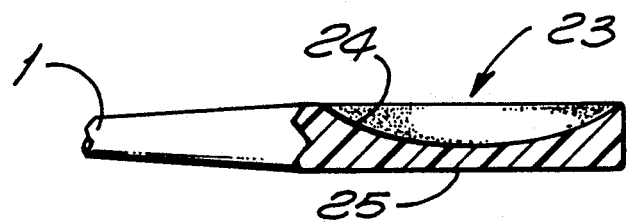
FIG. 6 is a view similar to FIG. 5 illustrating yet another alternative embodiment of the oral cleaning apparatus in accordance with the present invention.

Now referring to FIG. 5 a portion of an alternative embodiment oral cleaning device is illustrated. In this embodiment, the scoop tool 3 has been replaced by scoop tool 13 having two surfaces 14 and 15. Scoop tool 13 is different from scoop tool 3 in that both surfaces, 14 and 15, are concave. The double-concave shape may provide better scooping action in some circumstance. FIG. 6 illustrates a scoop tool 23 in which one surface 24 of the tool is concave, while the other surface 25 is flat. Again, the alternative scoop tools may be molded as a single device with the rigid shaft 1, or optionally comprise a softer material and be affixed to the shaft.

Figure 7:
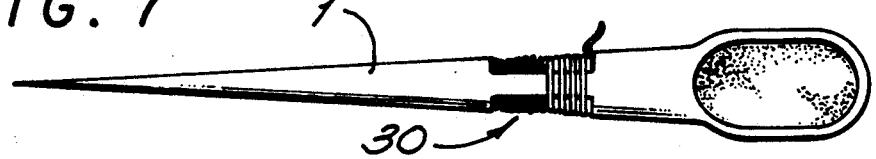
FIG. 7 illustrates another alternative embodiment of the oral cleaning apparatus in accordance with the present invention.
Figure 8:
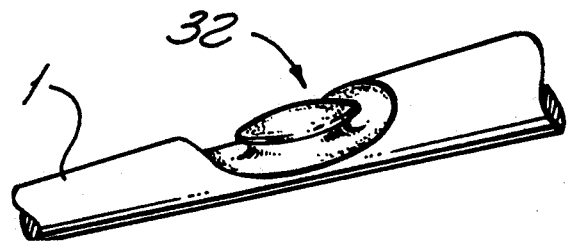
FIG. 8 illustrates yet another alternative embodiment of the oral cleaning apparatus in accordance with the present invention.

In addition to the cleaning tools described above, FIGS. 7 and 8 illustrate the composite oral cleaning apparatus of the present invention incorporating still another useful mechanism. The additional mechanism illustrated in both figures is for holding a supply of dental floss which may be used by the holder of the tool for cleaning between teeth and massaging the gums. In FIG. 7, the rigid shaft 1 is notched around its circumference such that the cut-away section 30 provides a spool around which a quantity of floss may be wrapped without increasing the diameter of the shaft. The floss holding mechanism illustrated by FIG. 8 comprises a region dug into one edge of the rigid shaft 1 thus forming a cleat 32 around which a segment of dental floss may be wrapped, again, without increasing the overall size of the oral cleaning apparatus.

The composite cleaning device described herein may be manufactured in any number of colors. Further, flavoring may be added to the materials when the cleaning device is produced to further enhance the cleaning process.

While the present invention has been described in terms of various embodiments, other embodiments will surely come to mind to those skilled in the art. For example, the various embodiments described have all incorporated a rigid shaft 1 as the support and holding mechanism for the present invention. It may prove desirable in some cases to provide the shaft 1 with some flexibility for reaching otherwise unreachable regions inside the mouth. Such a flexible shaft could be manipulated by the user by pressing a thumb against the shaft to bend it to the desired angle. Further, it may be desirable for handling purposes to provide the shaft 1 with a more circular or rectangular cross-section instead of an elliptical one. Those skilled in the art may envision other alternatives which do not depart from the spirit and scope of the present invention. The invention should, therefore, be measured in terms of the claims which follow.

I claim:

1. A composite oral cleaning apparatus comprising:
   an elongated, substantially solid shaft having first and second ends; and
   recessed floss holding means cut into said elongated shaft for securing a length of dental floss without increasing the diameter of said shaft when said dental floss is wrapped around said recessed floss holding means, said floss holding means sized to accomodate multiple turns of floss when wrapped therearound;
   said first end of said elongated shaft comprising a pick cleaning means, said pick cleaning means having a pointed tip;
   said second end of said elongated shaft comprising a scooping means, said scooping means having first and second surfaces wherein at least one of said surfaces is concave.

2. The composite oral cleaning apparatus of claim 1 wherein said elongated shaft is rigid and tapers from said second end to said first end.

3. The composite oral cleaning apparatus of claim 2 wherein said elongated shaft has an elliptical cross section.

4. The composite oral cleaning apparatus of claim 3 wherein said first surface of said scooping means is concave and said second surface of said scooping means is convex.

5. The composite oral cleaning apparatus of claim 3 wherein said first surface of said scooping means is concave and said second surface of said scooping means is concave.

6. The composite oral cleaning apparatus of claim 3 wherein said first surface of said scooping means is concave and said second surface of said scooping means is flat.

7. The composite oral cleaning apparatus of claim 2 wherein said elongated shaft has a rectangular cross section.

8. The composite oral cleaning apparatus of claim 2 wherein said elongated shaft has a circular cross section.

9. The composite oral cleaning apparatus of claim 2 wherein said pick cleaning means and said scooping means are composed of materials less rigid than said elongated shaft.

10. The composite oral cleaning apparatus of claim 1 wherein said recessed floss holding means comprises a portion of said elongated shaft cut away to provide a spool around which floss may be wrapped.

11. The composite oral cleaning apparatus of claim 1 wherein said recessed floss holding means comprises a portion of said elongated shaft notched on one edge to provide a cleat around which floss may be wrapped.

12. The composite oral cleaning apparatus of claim 1 wherein said shaft comprises a flexible material so that it may be bent to facilitate reaching otherwise inaccessible recesses in the mouth.

13. The composite oral cleaning tool of claim 1 further comprising flavoring carried by said tool.

14. A composite oral cleaning apparatus comprising an elongated substantially solid shaft having first and second ends, said elongated shaft having an elliptical cross section and tapering from said second end to said first end, said first end of said composite oral cleaning apparatus comprising a pointed tip for cleaning between teeth, said second end of said composite oral cleaning apparatus comprising a scooping means for cleaning other areas of the mouth, said scooping means having first and second surfaces wherein said first surface is concave and said second surface is convex, said elongated shaft including a recessed floss holding means for securing a length of dental floss; said floss holding means sized to accomodate multiple turns of floss when wrapped therearound.

15. The composite oral cleaning apparatus of claim 14 wherein said recessed floss holding means comprises a portion of said elongated shaft cut away to provide a spool around which floss may be wrapped.

16. The composite oral cleaning apparatus of claim 14 wherein said recessed floss holding means comprises a portion of said elongated shaft notched on one edge to provide a cleat around which floss may be wrapped.

* * * * *